United States Patent [19]
Bolduc et al.

[11] 4,126,134
[45] Nov. 21, 1978

[54] DISPENSING INSTRUMENT

[75] Inventors: Lee R. Bolduc, Minneapolis; Eugene A. Dickhudt, St. Paul, both of Minn.

[73] Assignee: Population Research Incorporated, Clearwater, Fla.

[21] Appl. No.: 543,876

[22] Filed: Jan. 24, 1975

Related U.S. Application Data

[63] Continuation of Ser. No. 369,710, Jun. 13, 1973, abandoned.

[51] Int. Cl.² .............................................. A61M 1/00
[52] U.S. Cl. ................................ 128/235; 128/349 B
[58] Field of Search ............... 128/235, 232, 221, 215, 128/218 N, 2.05 D, 2 F, 234, 240, 246, 349, 260, 341, 127, 129, 1 R

[56] References Cited

U.S. PATENT DOCUMENTS

| | | | |
|---|---|---|---|
| 2,541,520 | 2/1951 | Kegel | 128/235 |
| 2,696,212 | 12/1954 | Dunmire | 128/216 |
| 2,854,982 | 10/1958 | Pagano | 128/349 BU |
| 3,211,151 | 10/1965 | Foderick et al. | 128/349 B |
| 3,380,448 | 4/1968 | Sadove et al. | 128/215 |
| 3,394,705 | 7/1968 | Abramson | 128/349 B |
| 3,401,689 | 9/1968 | Greenwood | 128/129 |
| 3,422,813 | 1/1969 | Braley, Jr. et al. | 128/1 R |
| 3,448,739 | 6/1969 | Stark et al. | 128/2.05 D |
| 3,459,175 | 8/1969 | Miller | 128/349 B |
| 3,640,268 | 2/1972 | Davis | 128/232 |
| 3,680,542 | 8/1972 | Cimber | 128/1 R |

OTHER PUBLICATIONS

"The Effect of Methyl Cyanoacrylate Tissue Adhesive on the Human Fallopian Tube and Endometrium," by Stevenson, et al., The Journal of Obstetrics and Gynaecology of the British Commonwealth, Nov. 1972, vol. 79, pp. 1028-1039.

*Primary Examiner*—John D. Yasko
*Attorney, Agent, or Firm*—Lew Schwartz; Joseph F. Breimayer

[57] ABSTRACT

A dispensing instrument and method for simultaneously injecting fluids, as drug materials, into the canals of the Fallopian tubes of a female primate. The dispensing instrument has a body accommodating a container for storing the drug materials. An elongated member carrying an expandable balloon is mounted on the body. A sheath encloses the elongated member and balloon. The sheath is attached to a tubular needle which extends through the elongated member. A releasable lock holds both the sheath and needle in assembled relation with the body. A plunger moves the container into dispensing relation with the needle whereby the fluid in the container is carried via the needle into the uterine cavity. The fluid flows into the canals of the Fallopian tubes. The expandable member is subjected to fluid under pressure. The fluid is continuously monitored to maintain a continuous and uniform low pressure on the expanded balloon.

44 Claims, 18 Drawing Figures

DISPENSING INSTRUMENT

RELATED CASES

This application is a Continuation of Ser. No. 369,710 filed June 13, 1973 now abandoned entitled "Dispensing Instrument."

BACKGROUND OF THE INVENTION

Bilateral disection of Fallopian tubes is a common surgical procedure to sterilize a female primate. This procedure involves severing and tying the Fallopian tubes. Intrauterine devices, as plugs and wires, are used to temporarily sterilize a female. These devices include plugs which are inserted into the canals of the Fallopian tubes to prevent ova from passing from the canals into the uterus. Smith in 1849 described a method to treat sterility by passing whale bone splints into the canals. These devices do not insure that the ova cannot flow through the canals into the uterus. The devices can be dislodged and lost without the female being aware of it. There is no assurance that the devices are effective. Climber in U.S. Pat. Nos. 3,675,639 and 3,680,542 discloses plugs attached to the uterine wall to block the entrance of ova into the uterus from the Fallopian canals and the exit of sperm from the uterine cavity into the Fallopian canal. These plugs are designed to effect temporary sterilization in that they can be removed and do not permanently block the canals of the Fallopian tubes. Plug contraceptive devices are not entirely effective in that it is possible for ova to by-pass the plugs and enter the uterus. p Liquid tissue adhesives have been developed which polymerize when applied to moist living tissue. These adhesives have been used for various surgical procedures. When the tissue adhesives are used, the cells adjacent the tissue are damaged and eventually replaced with a fibrous tissue. A liquid tissue adhesive has been injected into the uterine cavity with a catheter to occlude the canals of the Fallopian tubes. Studies have been conducted with silver nitrate, zinc chloride and methyl cyanocrylate to occlude the canals of the Fallopian tubes. These catheters are not designed to accommodate the different sizes, shapes and characteristics of the uteri. Some of these catheters which use balloons are described in "The Effect of Methyl Cyanoacrylate Tissue Adhesive on the Human Fallopian Tube and Endometrium," by Stevenson, et al, *The Journal of Obstetrics and Gynaecology of the British Commonwealth*, November, 1972, Vol. 79, pp. 1028–1039, *Human Sterilization* edited by Richart and Prager, 1972, and *Female Sterilization*, edited by Duncan, et al, 1972 (See p. 107 e.g.).

SUMMARY OF THE INVENTION

The invention is directed to an apparatus and method for dispensing a fluid, as a drug material, into the Fallopian tube to treat and occlude the canals. The apparatus has an elongated catheter having a forward end adapted to be inserted into the uterine cavity. The forward end of the catheter has an expandable sleeve which displaces the uterine cavity. The sleeve is inflated at a relatively low pressure. The pressure of the fluid in the sleeve is continuously monitored whereby the sleeve fills the uterine cavity regardless of the shape, size or condition of the uterine cavity with a relatively low pressure. There is a minimum amount of back pressure to expand the sleeve. This pressure is sufficient to hold the sleeve in surface engagement with the inside wall of the uterus.

The catheter is attached to a housing means having a chamber for accommodating a container for storing the drug material. A sheath, shroud or cover encloses the elongated member and expandable sleeve. A tubular needle attached to the cover extends through the catheter. Latch means holds the needle and sheath in assembled relation with the housing means. The latch means is operable to release both the cover and needle. The cover is a relatively inexpensive and disposable item which can be readily replaced. The cover prevents contamination of the uterine cavity from any leakage of the fluid which expands the sleeve member. The container is moved into operative relation with the needle with a plunger movably mounted in the housing. The plunger is moved into the housing to force the container into the needle. The drug material in the container flows via the needle into the uterine cavity. The expanded sleeve confines the drug material to the upper part of the uterine cavity whereby the drug material flows into the Fallopian tubes. Substantially all of the material is moved into the Fallopian tubes since the expanded sleeve fills the uterine cavity and exerts a relatively low and uniform pressure on the side wall and top wall of the uterine cavity. The result is that there is a minimum amount of residual drug material left in the uterine cavity. A drug material, as a tissue adhesive, reacts with the moisture in the tissue of the Fallopian tubes to polymerize the adhesive and thereby occlude the canals. Other types of fluids can be injected into the canals of the Fallopian tubes to kill the tissue of the canal lining. This tissue is replaced with scar tissue which occludes the canals. The catheter is removed from the uterine cavity after the sleeve is deflated by allowing the fluid to exhaust from the chamber surrounded by the sleeve.

Figures 1, 2, 3, 4:
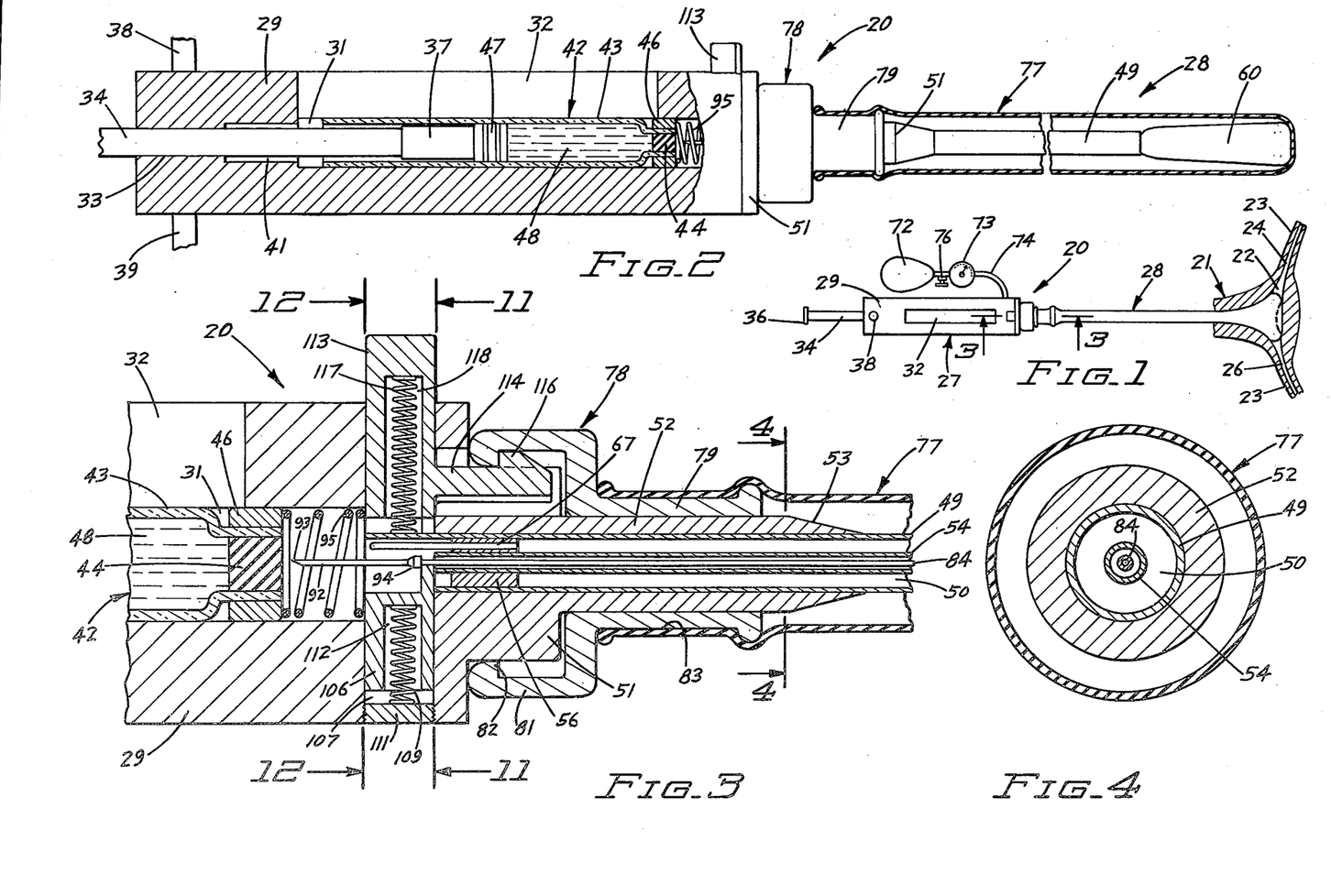
FIG. 1 is a top plan view of the dispensing instrument in operative association with a primate uterus.
FIG. 2 is a side elevational view, partly sectioned, of the dispensing instrument.
FIG. 3 is an enlarged sectional view taken along line 3—3 of FIG. 1.
FIG. 4 is an enlarged sectional view taken along line 4—4 of FIG. 3.

Referring to the drawings, there is shown in FIG. 1 the dispensing instrument indicated generally at 20 in operative relation with the uterus 21 of a primate female. Uterus 21 is a pear-shaped, thick walled, hollow organ situated between the bladder and rectum.

The uteri of primate females vary in size and shape. The wall thicknesses of uteri also vary, as well as their sensitivity to pain. The inner wall of the uterus may contain lymph nodes and vary in size and configuration. The uterine cavities of uteri vary in size and shape. Also, the elastic characteristics of the uteri walls differ. Some uteri have walls that are strong. Other uteri are weak and readily expandable.

Uterus 21 has a uterine cavity 22 which is flattened and generally triangular in shape. Leading to the upper part of opposite sides of the uterus 21 are Fallopian tubes 23 and 24. The Fallopian tubes are paired, trumpet-shaped, muscular linear members which extend from the superior angles of the uterine cavity to the ovaries (not shown). Fallopian tubes 23 and 24 each have a canal or aqueduct 25 and 26 respectively. The Fallopian tubes are musculomembranous structures about 12 cm in length. The location of the Fallopian tubes relative to the uterus can vary. Also, the size of the canals or oviducts of the Fallopian tubes can vary from female to female. They are commonly divided into an isthmus, an intramural and ampullary sections. The canals 25 and 26 provide passages for movement of ova from the ovaries into the uterine cavity 22. The intramural sections of the Fallopian tubes traverse the uterine wall in more or less straight fashion. It has an ampulla-like dilation just before it communicates with the uterine cavity 22. The canals 25 and 26 are narrowest at the intramural sections. The walls of the Fallopian tubes consist of three layers: the serosal layer, the muscular layer and a mucosal lining. The muscular layer includes longitudinal muscle fibers which, when contracted, bring the ends of the Fallopian tubes into close contact with the surfaces of the ovaries. Blood vessels are abundant in the muscular layer where they form with the muscle bundles a kind of erectile tissue which, if engorged, move the Fallopian tubes to sweep over the surfaces of the ovaries. This movement of the Fallopian tubes is impaired when the tubes are severed and tied. The occluding of the canals 25 and 26 with drug materials according to the invention does not interfere with the erectile action and movement of the Fallopian tubes relative to the ovaries.

Dispensing instrument 20 is an intrauterine catheter operable to direct a fluid, as drugs, tissue adhesive, or other material, into canals 25 and 26 of the Fallopian tubes. The tissue adhesive can be a cyanoacrylate, silver nitrate, quinacrine material and like materials used as surgical glues. The cyanoacrylate is a liquid plastic which sets up or polymerizes in response to moisture and thereby functions to occlude the canals of the Fallopian tubes. The cyanoacrylates include but are not limited to methyl cyanoacrylate, methyl-2-cyanoacrylate, ethyl cyanoacrylates, n-propyl cyanoacrylates, n-butyl cyanoacrylates, n-amyl cyanoacrylates, n-hexyl cyanoacrylates, n-heptyl cyanoacrylates, isobutyl-2-cyanoacrylates and n-octyl cyanoacrylates. The drugs can be of the type that temporarily block or occlude the canals of the Fallopian tubes. After a period of time, the canals will reopen to resume their normal function.

The instrument 20 has a dispensing unit indicated generally at 27 attached to an elongated probe or member 28 for transporting the fluid from the dispensing unit into the uterine cavity 22. The elongated member 28 has a length sufficient to extend through the vaginal cavity into the uterine cavity 22.

Referring to FIGS. 1 and 2, dispensing unit 27 has an elongated body 29 having a longitudinal chamber 31. A slot 32 extended along the top of the body is open to chamber 31. A longitudinal passage 33 in the rear portion of body 29 slidably accommodates a plunger 34. Plunger 34 has an outer disc-shaped end 36 and an inner forward head 37. A pair of outwardly directed projections 38 and 39 extend in opposite directions from the rear portion of body 29. Projections 38 and 39 function as finger grips when the thumb engages the disc 36 to move the plunger 34 into chamber 31. The body 29 has a recess 41 adjacent the inner end of passage 33 of a size to accommodate the head 37. The plunger 34 can be moved to a retracted or out position to locate the head in recess 41. This removes the plunger from chamber 31, providing full access into the chamber through slot 32.

A container or ampulla, indicated generally at 42, for storing the fluid is located in chamber 31. The container 42 can be loaded into chamber 31 through slot 32. Container 42 has an elongated cylinder 43 having a forward end closed with a plug 44. Plug 44 is of a resilient pierceable material, as rubber or the like, which can be penetrated with a needle. A band 46 surrounds the forward end of the cylinder 43. A sealing plug 47 closes the rear portion of cylinder 43 to confine the fluid 48 within the cylinder. The head 37 of the plunger is of a size to fit into the cylinder 43 and engage plug 47. The force applied to plunger 34 will move the sealing plug 47 into cylinder 43 and move the entire cylinder 43 in a forward direction.

Elongated probe 28 has a linear tubular support 49 having a longitudinal passage 50. As shown in FIG. 3, support 49 extends through an opening in a base 51 attached to the front of body 29. The forward end of base 51 is a longitudinal sleeve having an inclined ramp or cone-shaped surface 53. A longitudinal guide tube 54 is located concentrically within the tube 49. An end member or plug 56 closes passage 50 and supports the tube 54 in support 49.

Figures 5, 6, 7:
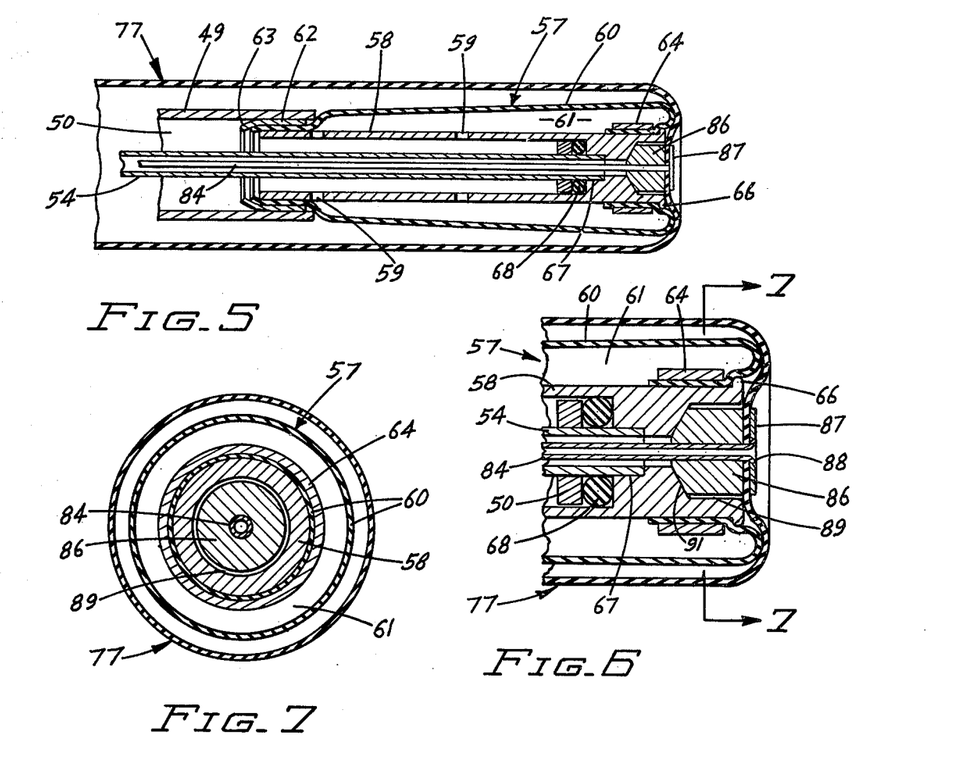
FIG. 5 is a longitudinal sectional view of the uterus or forward end of the dispensing instrument.
FIG. 6 is an enlarged sectional view of the forward end of the dispensing instrument.
FIG. 7 is a sectional view taken along line 7—7 of FIG. 6.

Referring to FIGS. 5, 6 and 7, an expandable balloon assembly, indicated generally at 57, is mounted on the outer end of support 49. Balloon assembly 57 is a replaceable unit. Balloon assembly 57 has an elongated inner sleeve 58 open at one end to the passage 50. The sleeve 58 has a plurality of holes 59 which permit fluid to flow through the sleeve 58. An annular flexible sheet member or cover 60 surrounds sleeve 58 and forms an annular chamber 61 for accommodating fluid, as air or a liquid, to expand the cover 60. Cover 60 is a cylindrical sheet member of flexible and elastic material which expands with a minimum of elongation of the material. For example, thin latex rubber can be used as a cover material. A band 62 clamps the inner end of cover 60 to the sleeve 58. The band 62 has an inwardly directed annular lip which permits the sleeve to be guided into concentric and sealing relation with the end of tubular support 49. The outer end of cover 60 is mounted on sleeve 58 with a band 64. The outer end of sleeve 58 has an outwardly directed annular flange 66 which prevents band 64 from sliding off the end of sleeve 58. The outer end of guide tube 64 is located in a recess 67 in the outer end of sleeve 58. An O-ring 68 surrounding guide tube 54 serves as a seal between the outer end of guide tube 54 and the sleeve 58.

Figures 8, 11, 12, 13:
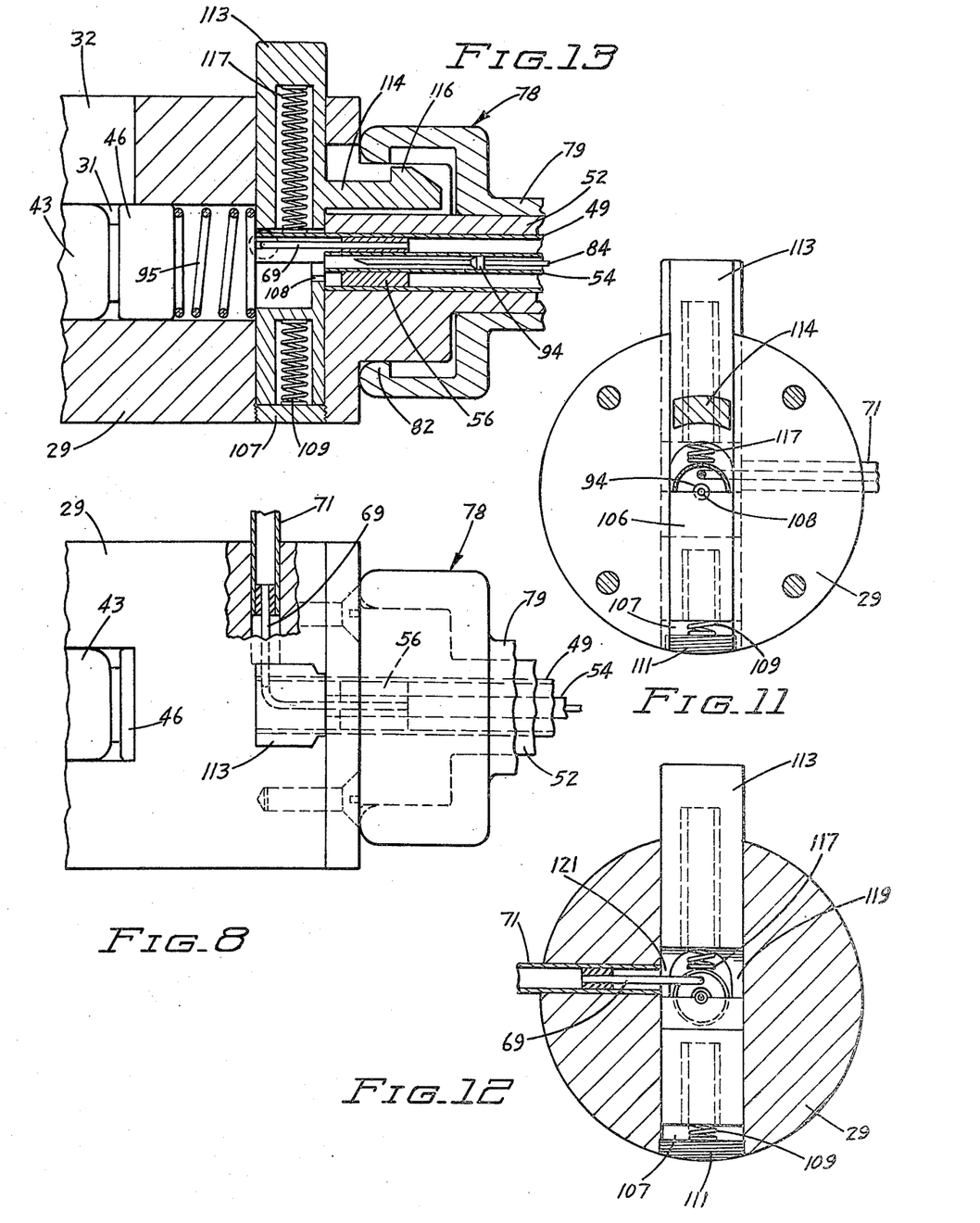
FIG. 8 is a top plan view of the mid-section of the dispensing instrument.
FIG. 11 is a sectional view taken along line 11—11 of FIG. 5.
FIG. 12 is a sectional view taken along line 12—12 of FIG. 3.
FIG. 13 is a sectional view similar to FIG. 3 showing the lock structure in the release position.

Referring to FIGS. 1 and 8, a tube 69 located in the forward end of body 29 extends through the plug 56 to provide a passage to passage 50 of support 49. The opposite end of tube 69 is joined to a short nipple 71. Air is supplied to nipple 71 with a collapsible bulb pump 72. Pump 72 is connected to a pressure gauge 73 and a line 74 joined to nipple 71. A releasable valve 76 is operable to evacuate the air from the system. Pump 72 can be a syringe or cylinder piston-type to supply air to the system. Other fluids, as water, can be used to inflate cover 60. The pump 72 is operated to deliver air to the passage 50. The air in passage 50 flows through holes 59 into the chamber 61. The cover 60, being flexible material, will expand to fill the uterine cavity 22, as shown in FIG. 1.

As shown in FIGS. 2 and 3, a replaceable and disposable shroud, cover or sheath indicated generally at 77 surrounds the tubular support 49 and flexible sheet member 60. The shroud 77 is an elongated flexible balloon member made of material having a low surface tension, as latex rubber. The shroud 77 is attached to a connector 78 releasably mounted on the forward end of the body 29. Connector 78 has a forwardly directed collar 79 slidably disposed on the sleeve 52. Collar 79 is joined to a circular head 81 having an inwardly directed annular lock lip 82 operative to coact with latch structure, hereinafter described, to releasably hold the collar on the body 29. The shroud 77 is located over the collar 79 and attached thereto with adhesive 83 or similar bonding material.

An elongated tubular needle 84 is longitudinally located within the shroud 77. As shown in FIGS. 5 and 6, the outer end of the needle 84 is attached to the end of shroud 77 with an inside member 86 and an outside washer 87. The end of needle 84 has a flared portion or outwardly directed beveled portion 88 cooperating with washer 87 to clamp the members 86 and 87 on the end of shroud 77. Washer 87 is located in a central recess surrounded by sleeve member 60. The recess provides a space for the fluid material delivered by the needle and distributes the pressure of the fluid material on the fundus. The inside member 86 is disposed in a circular recess 89 in the outer end of inside sleeve 58. The bottom of member 86 and the bottom of recess 89 have cooperating cone-shaped faces 91 which position and center member 86 on the inside sleeve 58. The inner end of needle 84 has an end section 92 projected into the chamber 31. As shown in FIG. 3, end section 92 terminates in a point 93 aligned with the front plug 44 of the container 42. End section 92 has a stop shoulder 94 which holds the needle in assembled relation with body 29 and holds the outer end of the shroud in assembled relation with sleeve 58.

Figure 9:
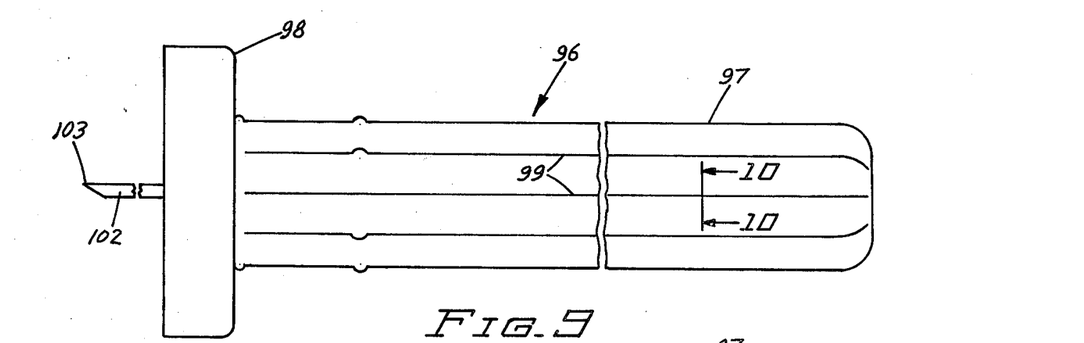
FIG. 9 is a side elevational view of a modified shroud for the dispensing instrument.
Figure 10:
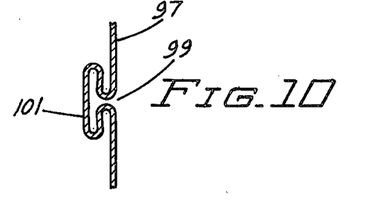
FIG. 10 is an enlarged sectional view taken along line 10—10 of FIG. 9.

Referring to FIGS. 9 and 10, there is shown a modification of the disposable shroud indicated generally at 96. Shroud 96 is an elongated flexible tubular member made of sheet material 97, such as polystyrene film, relaxed elastic rubber, and the like. The sheet material 97 has a closed forward end and an open rear end. A connector 98 is attached to the open end. Connector 98 is identical to connector 97 shown in FIGS. 2 and 3. The sheet material 97 has a plurality of longitudinal pleats 99 which permit the shroud 96 to expand without increasing the surface tension or expanding the sheet material. As shown in FIG. 10, the pleats 99 are formed by folding back longitudinal portions 101 whereby the circumference of the tubular sheet material can be increased without subjecting the sheet material to tension. An elongated tubular needle 102 is located longitudinally in the shroud. The outer end of the needle is attached to the end of the shroud. The structure to attach the needle to the shroud is identical to the inside member 86 and washer 87, as shown in FIG. 6. Needle 102 has an end section which projects outwardly from the connector 98 and terminates in point 103.

Figure 14:
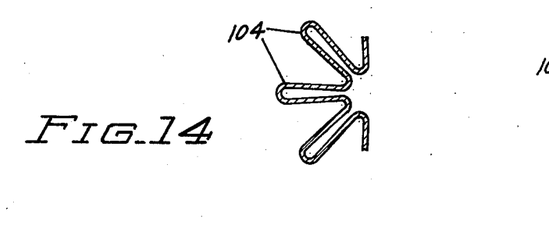
FIG. 14 is a view similar to FIG. 10 of a modified pleat arrangement.

A modification of the pleat arrangement of the sheet material forming the shroud is shown in FIG. 14. The sheet material has a plurality of radial folds 104. Folds 104 are circumferentially spaced around the shroud and extend longitudinally as pleats 99 in FIG. 9. The radial length of the pleats can vary whereby the expanded shape of the shroud can be controlled. For example, the radial length of the pleats at the outer section of the shroud can be longer than the radial length of the pleats at the inner section. The expanded shroud has a generally pear shape.

Referring to FIGS. 3, 11 and 12, a holding member 106 engages stop shoulder 94 on the needle 84 to hold the needle 84 in assembled relation with the guide tube 54. Holding member 106 is located in an upright position in a groove 107 in the forward part of body 29. The top part of member 106 has a recess 108 to accommodate a portion of needle 84 behind the stop shoulder 94. A spring 109 biases the member 106 into engagement with the needle. Spring 109 is located in a bore 112 in the holding member 106. A plug 111 closing the groove 107 provides an anchor for spring 109.

Located opposite the holding member 106 is a manually movable actuator 113. Actuator 113 has a forwardly directed arm 114 terminating in an upwardly directed finger 116. Finger 116 engages the inwardly directed lip 82 to hold the connector 78 in assembled relation with the body 29. A spring 117 biases the actuator 113 in an outward direction. The spring is located in a bore 118 and is anchored on a portion of the tubular support 49. As shown in FIG. 12, the actuator 113 has a pair of spaced downwardly directed legs 119 and 121 which engage the top of the holding member 106. When a downwardly or inwardly directed force is applied to the actuator 113, the finger 116 will move inwardly away from lip 82, as shown in FIG. 13. This permits the connector 78 to be removed from the sleeve 52. Legs 119 and 121 bearing on holding member 106 move the holding member in a downward direction against the biasing force of spring 109. This releases the holding member 106 from the stop shoulder 94 whereby the needle 84 can be removed from its fixed position, as shown in FIG. 3. When the needle 84 is in the fixed position, the inside member 86 shown in FIGS. 5 and 6 is in the in or stop position with the cone faces 91 in engagement with each other.

In use, the dispensing instrument 20 is initially loaded with a container or ampulla 42. The plunger 34 is withdrawn until head 37 is located in recess 41. The container 42 is loaded into the chamber 31 by moving the container through the slot 32. The plunger 34 is moved to a forward position until the head 37 engages the sealing plug 47. This locates the head 37 in a portion of the cylinder 43, thereby maintaining the cylinder 43 in the chamber 31. The front plug 44 is aligned with the needle 84. The spring 95 holds the plug in a spaced relation with respect to the needle.

The shroud 77 can be packaged in a separate sterile container. One end of this container is open whereby the shroud 77 is permitted to be placed on the tubular support 49. The shroud and needle 84 are packaged together and are a disposable and sterile assembly. The forward end of the needle is inserted into the guide tube 54. The connector and needle are moved into the tubular support 49 until the connector 78 is positioned on sleeve 52. The lip 82 of the connector is moved over the finger 116 until the finger 116 locks the connector onto the body or housing 29. The outer end of the shroud 77 is moved until the inner member 106 is located in the recess 89. This moves the stop shoulder 94 past the holding member 106 whereby the holding member fixes the position of the needle with respect to the guide tube 54.

The hose 74 is connected to the nipple 71 whereby the collapsible member 72 is operable to provide air under pressure to chamber 50. The tube 74 can be initially applied to the nipple before the container is loaded in the housing.

In use, the container or package for the shroud is removed from the shroud. The shroud along with the tubular support within the shroud is introduced through the cervical opening into the uterine cavity. The pump 72 is actuated to provide air under pressure to the passage 50. The air in passage 50 flows through openings 59 into chamber 61. This expands the flexible sheet member, increasing its size. The flexible sheet member expands the outer end of the shroud to displace the uterine cavity. The shroud is of a low tension elastic material which places a uniform and low pressure on the inner wall of the uterus. The shroud and flexible sheet member assume the shape of the uterine cavity and position the end of the shroud adjacent the upper end of the uterus. The sleeve member 60 is expanded with air under pressure to a predetermined pressure, as indicated by gauge 73. Gauge 73 continuously monitors the pressure of the air expanding the sleeve member 60. This continuous monitoring of the air insures that there is substantially uniform pressure on the inside walls of the utuerus and that the sleeve member displaces the uterine cavity. Also, the monitoring of the air pressure insures that there is no leakage in the sleeve member 60 and the passage leading to the sleeve member 60.

The drug material 48 in the container 42 is injected into the uterine cavity between the expanded shroud and the inside wall of the uterus. The body 48 is grasped by gripping projections 38 and 39 and forcing the plunger 34 into the chamber 31. The head 37, being in engagement with the end plug 47, forces the container 42 toward needle 84. The end section 92 of the needle pierces the end plug 44 whereby the drug material 48 can flow through the passage in the needle to the outer end of the shroud. The needle, as it passes through plug 44, is wiped clean. The drug material will flow between the shroud and the upper portion or fundus of the uterus into the Fallopian canals 24 and 26. The drug material can be a tissue adhesive, as cyanoacrylate monomer. The drug material causes fibroblastic proliferation which in time will histologically close the canals of the Fallopian tubes. When the plunger 34 has moved the plug 47 into the head of cylinder 43, the drug material 48 has been dispensed through needle 84 into the uterine cavity.

The instrument 20 is removed from the uterine cavity by initially relieving the pressure of the air from the sleeve member 60. This is accomplished by opening valve 76. With the release of pressure, the size of sleeve member 60 is reduced whereby the shroud can be withdrawn from the uterine cavity. The shroud 77 is then released from body 29 by pressing and moving the manual actuator 113 into the body. This releases finger 116 from the lip 82 and the holding member 106 from the stop shoulder 94. The shroud 77 along with the needle 84 can then be removed from the support tube 49.

Figures 15, 16, 17, 18:
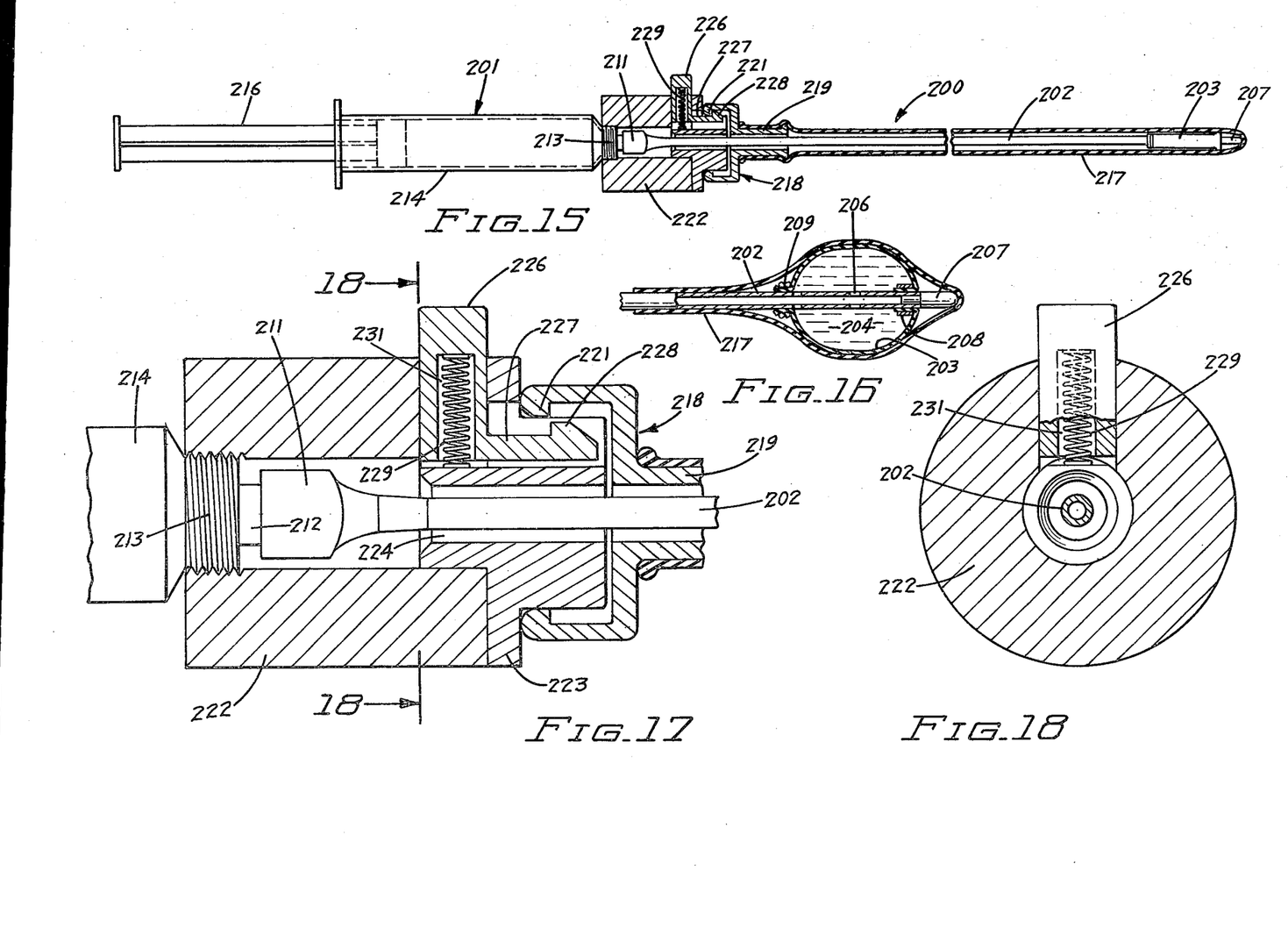
FIG. 15 is a side elevational view, partly sectioned, of a catheter attached to a syringe and enclosed in a disposable shroud.
FIG. 16 is an enlarged sectional view of the forward end of the catheter.
FIG. 17 is an enlarged sectional view of the lock structure for the shroud.
FIG. 18 is a sectional view taken along line 18—18 of FIG. 17.

Referring to FIG. 15, there is shown an elongated flexible catheter indicated generally at 200 attached to a syringe 201. The catheter 200 has an elongated flexible tube 202. An expandable sleeve or balloon 203 is mounted on the outer end of tube 202. Sleve 203 surrounds a chamber 204 in communication with the inside of tube 202 through a plurality of holes 206. As shown in FIG. 16, a cap 207 closes the outer end of tube 202. A band 208 attaches the outer end of sleeve 203 to the tube 202. A tie 209, as cord or the like, attaches the inner end of the sleeve to the tube. A bonding material, as adhesive, can be used to secure the expandable sleeve 203 to the tube 202. The sleeve 203 is made of flexible and expandable sheet material, as rubber.

As shown in FIGS. 15 and 17, a head 211 is at the proximal end of the cathetor 200. The head 211 has an outwardly directed neck 212 that is threaded into a nipple 213. The nipple 213 is at the forward end of a cylinder 214. A plunger 216 is slideably disposed in the cylinder to displace a fluid in the cylinder into the tube 202 of the catheter. Movement of the plunger into the cylinder forces the fluid into the catheter to expand the sleeve 203 as shown in FIG. 16.

The catheter 202 is enclosed within a sheath or cover 217. The sheath is of expandable material, as rubber, plastic or the like, and has a generally tubular shape with a closed outer end. A connector 218 is attached to the inner end of the sheath 217. The connector has a collar 219 carrying the inner end of sheath 217 and a head having an inwardly directed lip 221. The sheath 217 and connector 218 are low cost, disposable assemblies that can be readily placed over the catheter and attached thereto with a releasable lock assembly hereinafter described. A housing or body 222 is attached with threads to the nipple 213. Body 222 has a forward section 223. Section 223 has a longitudinal passage 224 for accommodating the tube 202. Slideably disposed in body 222 is a manually operated actuator 226. The actuator 226 has a forwardly directed arm 227. An upwardly directed finger 228 is attached to the outer end of the arm 227. Finger 228 cooperates with the lip 221 to hold the connector 218 in assembled relation with body 222. The manually operated actuator 226 is biased in an upward or outward direction by a spring 229. Spring 229 is located in inwardly open bore 231. The lower end of spring 229 engages a portion of the forward section 223 whereby the spring biases arm 227 and finger 228 in an outward direction into locking engagement with the lip 221. The actuator 226 together with its arm 227 and finger 228 function as a lock mechanism with lip 221 to releasably hold the connector 218 in assembled relation with body 222.

In use, the manually operated actuator 226 is depressed or moved into body 222. This releases the finger 228 from engaging and locking relation with lip 221.

The connector 218 can then be moved in a longitudinal direction and stripped from the tube 202. A new sheath and connector can be placed over tube 202 and held thereon with the finger 228.

While there have been shown and described several preferred embodiments of the dispensing instrument and fluid container, as well as the method of introducing material into the canals of the Fallopian tubes, it is understood that variations and changes in the structures and methods can be made by those skilled in the art without departing from the spirit of the invention. The invention is defined in the following claims.

The embodiments of the invention in which an exclusive property of privilege is claimed are defined as follows:

1. A dispensing instrument comprising: housing means having a chamber for accommodating a container storing material, an elongated member attached to said housing means, expandable means mounted on the elongated member, said expandable means including an elastic and flexible sleeve surrounding a chamber, sheath means enclosing the elongated member and expandable means, said sheath means including an elastic and flexible cover located over the sleeve, tubular needle means for delivering material from the container to the outside of the sheath means, means releasably connecting the sheath means to the housing means, and means to provide fluid under pressure to the chamber surrounded by the sleeve whereby fluid under low pressure within the chamber expands the sleeve and cover.

2. The instrument of claim 1 including: plunger means movably mounted on the housing means operable to move the container into the needle means.

3. The instrument of claim 1 wherein: the housing means has a slot open to the chamber whereby the container can be inserted into the chamber through said slot.

4. The instrument of claim 1 wherein: the expandable means has means operable to removably mount the expandable means on the elongated member.

5. The instrument of claim 4 wherein the needle means has means holding the expandable means in operative relation with the elongated member.

6. The instrument of claim 1 wherein: the means releasably connecting the sheath means to the housing includes lock means for holding the sheath means on the housing means.

7. The instrument of claim 6 wherein: the lock means includes means to hold the needle means in a fixed position with respect to the container.

8. The instrument of claim 1 wherein: the sheath means comprises an elongated flexible tubular means and connector means attached to the tubular means.

9. The instrument of claim 8 wherein: said housing means has a sleeve means, said connector means having a collar slidably located on the sleeve means.

10. The instrument of claim 8 including: lock means having a member engageable with the connector means to releasably hold the connector means on the sleeve means.

11. The instrument of claim 10 wherein: the member engageable with the connector means comprises a forwardly projected member having an upwardly directed stop portion, said connector means having lip means cooperating with the stop portion to releasably hold the connector means on the sleeve means.

12. The instrument of claim 11 including: means to bias the forwardly projected member toward the lip means.

13. The instrument of claim 10 wherein: the lock means has a second member engageable with the needle means to fix the position of the needle means relative to the housing means.

14. The instrument of claim 1 including: means attaching the tubular needle means to a portion of the sheath means.

15. The instrument of claim 1 including: means to monitor the pressure of the fluid expanding the expandable means.

16. The instrument of claim 1 including: means to continuously monitor the pressure of the fluid in the chamber surrounded by the sleeve.

17. A sheath for an elongated catheter comprising: an elongated flexible tubular means having a closed end and an open end, elongated tubular needle means extended longitudinally within the tubular means, said needle means having an end open adjacent to the outside of the closed end of the tubular means, means connecting a portion of the needle means to the closed end of the tubular means, and connector means attached to the open end of the tubular means, said connector means operable to cooperate with a part of the cathether to hold the sheath on the catheter.

18. The sheath of claim 17 wherein: the connector means has a sleeve, said open end of the tubular means mounted on the sleeve.

19. The sheath of claim 17 wherein: the connector means has a lip cooperating with part of the catheter to hold the sheath on the catheter.

20. The sheath of claim 17 wherein: the means connecting a portion of the needle means to the closed end of the tubular means includes a member located within the tubular means.

21. The sheath of claim 17 wherein: the tubular means is an elongated elastic and flexible sleeve.

22. A method of introducing a material into the canals of Fallopian tubes comprising:
   introducing an elongated catheter having an expandable sleeve through the cervical opening into the uterine cavity;
   expanding the sleeve with fluid under pressure to a predetermined pressure to displace the uterine cavity with the expanded sleeve,
   continuously monitoring the pressure of the fluid expanding the sleeve whereby the sleeve exerts a substantially uniform pressure on the inside walls of the uterus,
   dispensing material under pressure into the uterine cavity between the expanded sleeve and the inside wall of the uterus, said material under pressure moving toward and into the canals of the Fallopian tubes,
   releasing the pressure of the fluid from the sleeve to contract the sleeve, and
   withdrawing the catheter from the uterine cavity.

23. The method of claim 22 wherein: the fluid supplied to the sleeve is air under pressure.

24. The method of claim 22 wherein: the sleeve member is enclosed with a removable sheath.

25. The method of claim 22 wherein: the material is dispensed under pressure by moving a container storing the material into operative relation with a tubular needle, said needle delivering the material to the uterine cavity.

26. The method of claim 22 wherein: a tissue adhesive material is dispensed under pressure into the uterine cavity.

27. The method of claim 22 wherein: the material is discharged into the uterine cavity adjacent the center section of the funds.

28. The method of claim 22 wherein: the sleeve is an elastic and flexible sheet member expanded with fluid under low pressure.

29. An apparatus for placing material in the canals of Fallopian tubes of a femal comprising: means having an expandable sleeve member positionable in the uterine cavity, sheath means enclosing the expandable sleeve member, said sheath means including an elastic and flexible cover located over the sleeve member, means to expand the sleeve member and cover to displace the uterine cavity and place the cover in substantial uniform engagement with the side walls and fundus of the uterus, and means to dispense the material under pressure into the uterine cavity between the cover and the fundus, said material under pressure being directed toward and into the canals by the cover.

30. The apparatus of claim 29 wherein: the means to dispense the material has a material discharge opening positionable adjacent the central portion of the fundus whereby the material is discharged adjacent the central portion of the fundus.

31. The apparatus of claim 29 wherein: the expandable member is a sleeve member of flexible and elastic material.

32. The apparatus of claim 29 wherein: the means having an expandable member includes an elongated tube, said expandable member being releasably mounted on the tube.

33. The apparatus of claim 29 including: means to releasably mount the sheath means on the means having an expandable sleeve member.

34. The apparatus of claim 33 wherein: the means to releasably mount the sheath means includes lock means having a member to releasably hold the sheath means adjacent to the sleeve member.

35. The apparatus of claim 33 wherein: the means to dispense the material includes an elongated tubular member located within the sheath means, said tubular member having an outlet opening located outside of the sheath means.

36. The apparatus of claim 35 including: means to connect the tubular member to the sheath means.

37. An instrument comprising: housing means having a chamber for storing material, an elongated member attached to the housing means, expandable means mounted on the elongated member, said expandable means including an elastic and flexible sleeve surrounding a chamber, sheath means enclosing the elongated member and expandable means, said sheath means including an elastic and flexible cover located over the sleeve, means releasably connecting the sheath means to the housing means, and means to provide fluid under pressure to the chamber surrounded by the sleeve whereby fluid under low pressure within the chamber expands the sleeve and cover.

38. The instrument of claim 37 wherein: the means releasably connecting the sheath means to the housing means includes lock means for holding the sheath means on the housing means.

39. The instrument of claim 37 wherein: the sheath means includes an elongated flexible tubular means and connector means attached to the tubular means.

40. The instrument of claim 39 wherein: said housing means has a section accommodating a part of the connector means.

41. The instrument of claim 39 wherein: lock means having a member engageable with the connector means to releasably hold the connector means on the section.

42. The instrument of claim 41 wherein: the member engageable with the connector means comprises a forwardly projected member having an upwardly directed stop portion, said connector means having lip means cooperating with the stop portion to releasably hold the connector means on the sleeve means.

43. The instrument of claim 42 including: means to bias the forwardly projected member toward the lip means.

44. The instrument of claim 37 wherein: said housing means includes a syringe and a body releasably mounted on the syringe.

* * * * *